(12) United States Patent
Ueda et al.

(10) Patent No.: US 6,455,743 B1
(45) Date of Patent: Sep. 24, 2002

(54) PROCESS FOR PRODUCING ALCOHOLS

(75) Inventors: Akio Ueda; Yuichi Fujita; Atsuhiro Adachi; Hiroki Emoto, all of Okayama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/450,123

(22) Filed: Nov. 26, 1999

(30) Foreign Application Priority Data

Nov. 27, 1998 (JP) .......................................... 10-337351

(51) Int. Cl.$^7$ ............................................... C07C 29/14
(52) U.S. Cl. ........................ 568/881; 568/882; 568/451
(58) Field of Search ................................. 568/451, 454, 568/881, 882, 461, 462, 463, 464, 465

(56) References Cited

U.S. PATENT DOCUMENTS

| | | | |
|---|---|---|---|
| 3,098,101 A | 7/1963 | Aldridge et al. | |
| 4,762,817 A | 8/1988 | Logsdon et al. | 502/329 |
| 4,876,402 A | 10/1989 | Logsdon et al. | 568/881 |
| 5,302,569 A | 4/1994 | Horn et al. | 502/342 |
| 5,684,215 A | 11/1997 | Horn et al. | 568/881 |

FOREIGN PATENT DOCUMENTS

| | | |
|---|---|---|
| EP | 0 008 767 | 3/1980 |
| EP | 0 074 193 | 3/1983 |
| WO | WO 96/22264 | 7/1996 |

OTHER PUBLICATIONS

Chemical Abstracts, vol. 096, No. 7, 1 page, AN 96:51807, Feb. 15, 1982, BR 8 001 584, Sep. 22, 1981.

*Primary Examiner*—Sreeni Padmanabhan
(74) *Attorney, Agent, or Firm*—Oblon, Spivak, McClelland, Maier & Neustadt, P.C.

(57) ABSTRACT

A process for producing alcohols, which comprises subjecting a mixture comprising an aldehyde having from 2 to 5 carbon atoms and a polycondensate of the aldehyde at a weight ratio of from 95:5 to 5:95 to a mixing hydrogenation reaction in the presence of a catalyst to produce alcohols corresponding to the aldehydes at the same time wherein substantially no by-product is produced.

19 Claims, No Drawings

PROCESS FOR PRODUCING ALCOHOLS

BACKGROUND OF THE INVENTION

1. Field of the Invention

The present invention relates to a production process which comprises subjecting an aldehyde having from 2 to 5 carbon atoms and a polycondensate of the aldehyde to a mixing hydrogenation reaction to produce alcohols corresponding to each of these aldehydes at the same time. (As described herein, the term "corresponding to" means a particular aldehyde, when hydrogenated, necessarily results in a particular alcohol. For example, n-butyraldehyde, when hydrogenated, necessarily results in n-butanol.) More particularly, the present invention relates to a production process which comprises subjecting the two aldehydes as starting materials to a mixing hydrogenation reaction whereby the production of an ester compound and/or an ether compound as by-products is inhibited, making it possible to efficiently produce alcohols corresponding to each of the aldehydes at the same time.

2. Discussion of the Background

A process which comprises allowing an aldehyde to undergo a hydrogenation reaction (hereinafter occasionally referred to as "hydrogenation") has long been put in practical use on an industrial basis. For example, a process which comprises allowing n-butylaldehyde produced by the hydroformylation reaction of a propylene to undergo hydrogenation to produce n-butyl alcohol and a process which comprises allowing 2-ethyl-2-hexenal produced by the aldol condensation reaction of n-butyl aldehyde to undergo hydrogenation to produce 2-ethylhexanol have been widely known.

Such an industrial hydrogenation reaction of an aldehyde is carried out in either a liquid phase or a gas phase. In either reaction system, various side reactions occur to produce a large amount of by-products, lessening the reaction selectivity. One of the undesirable by-products of the hydrogenation reaction in the gas phase is an ester compound. For example, the reaction solution obtained by the gas phase hydrogenation reaction of n-butyl aldehyde contains butyl acetate as a by-product. Further, the reaction solution obtained by the gas phase hydrogenation reaction of 2-ethyl-2-hexenal contains the 2-ethylhexyl ester of 2-ethylhexanoic acid (2-ethylhexanoic acid-2-ethylhexyl) as a by-product. Known mechanisms of production of ester compound include a mechanism where a hemiacetal is produced from an aldehyde and an alcohol, and the hemiacetal then undergoes a dehydrogenation reaction to produce an ester compound, and a mechanism where two aldehyde molecules undergo a Tischenko reaction to produce an ester compound.

In order to inhibit the production of such an ester compound as a by-product, some approaches have heretofore been disclosed such as (I) a method involving the use of, as a hydrogenation catalyst, a reducing copper oxide-zinc oxide catalyst comprising a selectivity accelerator incorporated therein (an in Japanese Patent No. 2,655,034), (II) a method involving the hydrogenation reaction in the presence of a supported catalyst comprising nickel, aluminum oxide and zirconium dioxide incorporated therein (as in JP-B-6-4551 (The term "JP-B" as used herein means an "examined Japanese patent application")), (III) a method involving the hydrogenation reaction in the presence of a catalyst comprising copper, zinc oxide and aluminum oxide incorporated therein (as in JP-B-8-29249) and (IV) a method involving the hydrocracking of an ester produced as a by-product to effective components which are then recovered (as in JP-A-58-43930 (The term "JP-A" as used herein means an "unexamined published Japanese patent application")).

However, the foregoing methods (I) to (III) are disadvantageous in that they require the use of a catalyst having a certain special specification that adds to the production cost. Further, the foregoing method (IV) is disadvantageous in that a reactor for the decomposition of the ester is needed in addition to the reactor for the hydrogenation of aldehyde, adding to the construction cost. Accordingly, none of these methods are industrially effective.

Further, JP-A-6-1733 discloses a production process which comprises the hydrogenation reaction of an aldehyde having 5 or less carbon atoms to produce an alcohol, wherein 1-octa-2,7-dienol, which is an unsaturated alcohol having 8 carbon atoms, is present in the reaction system.

However, the above-discussed references do not describe or suggest the production process of the present invention which comprises mixing two aldehydes, i.e., an aldehyde having from 2 to 5 carbon atoms and a polycondensate of the aldehyde, and then subjecting the mixture to a hydrogenation reaction to produce two alcohols corresponding to the two aldehydes, respectively, at the same time on an industrial basis.

Further, the production process of the present invention has not even been practiced.

The term "mixing two aldehydes, i.e., an aldehyde having from 2 to 5 carbon atoms and a polycondensate of the aldehyde, and then subjecting the mixture to a hydrogenation reaction to produce two alcohols corresponding to the two aldehydes, respectively, at the same time on an industrial basis" as used herein is meant to indicate that an aldehyde having from 2 to 5 carbon atoms and a polycondensate of the aldehyde are mixed at a specified ratio, and then subjected to a hydrogenation reaction, but does not mean that a solution having such a composition as having unreacted raw aldehydes, e.g., 91.0% of 2-ethyl-2-hexenal and 1.6% of n-butyraldehyde as disclosed in JP-B-8-29249 is supplied at the step for condensation of aldehyde to undergo the hydrogenation reaction.

One of the reasons why the production process of the present invention for obtaining two alcohols by mixing and hydrogenating two different aldehydes has never been practiced is that when such a hydrogenation reaction is allowed to occur in the presence of two or more aldehydes, by-products which cannot be normally produced when these aldehydes are individually subjected to a hydrogenation reaction are produced, requiring much labor to remove in the purification system.

SUMMARY OF THE INVENTION

An object of the present invention is to provide a process for the production of alcohols which comprises inhibiting the production of an ester and/or ether as a by-product during the production of two alcohols to produce two desired alcohols at the same time to advantage on an industrial basis.

The inventors made extensive studies of the foregoing problems. As a result, it was found that when an aldehyde having from 2 to 5 carbon atoms and a polycondensate of the aldehyde are simultaneously supplied into the reaction system at a specified mixing ratio where they are then mixed and subjected to a hydrogenation reaction, the production of an ester compound as an undesirable by-product can be unexpectedly inhibited, the amount of an ether compound to be similarly produced can be considerably reduced and the percent production of alcohol can be enhanced, making it possible to simultaneously produce two alcohols to advantage on an industrial basis. The present invention has thus been worked out.

Two series of hydrogenation reaction systems have heretofore been required to hydrogenate two aldehydes and hence produce corresponding alcohols. The use of the process of the present invention makes it possible to unify the two series of hydrogenation reaction systems to one series. As a result, the reduction of the number of series of reaction system makes it possible to facilitate the industrial practice of this process.

The essence of the present invention is a process for the production of alcohols which comprises supplying an aldehyde having from 2 to 5 carbon atoms and a polycondensate of the aldehyde into the same reaction system at a weight ratio of from 95:5 to 5:95 where they are then mixed and subjected to a hydrogenation reaction in the presence of a catalyst to produce alcohols corresponding to the aldehydes (the aldehyde and the polycondensate thereof) at the same time.

DETAILED DESCRIPTION OF THE PREFERRED EMBODIMENTS

The present invention will be further described hereinafter.

As the aldehyde compounds to be used as a starting material in the mixing hydrogenation reaction of the present invention, there may be used an aldehyde having from 2 to 5 carbon atoms and a polycondensate thereof. Specific examples of such aldehyde compounds include propionaldehyde and a condensation dimer thereof, butyraldehyde and a condensation dimer thereof, and valeraldehyde and a condensation dimer thereof. Preferred among these compounds are butyraldehyde and a condensation dimer thereof.

Such aldehydes can be normally obtained by the hydroformylation of an olefinic compound having 4 or less carbon atoms. As the polycondensate thereof, there may be used an aldol condensate of such an aldehyde. A specific example of such an aldehyde compound and aldol condensate thereof includes butyraldehyde produced from propylene, and 2-ethyl-2-hexenal. The term "butyraldehyde" as used herein substantially means n-butyraldehyde which may contain a small amount of i-butyraldehyde.

The olefinic compound to be used as a starting material in the hydroformylation reaction does not need to be subjected to any special pretreatment before use. In practice, however, the olefinic compound may be subjected to ordinary adsorption, extraction, distillation, heat treatment, membrane separation or the like before use so that sulfur-containing compounds, halogen-containing compounds, dienes, trienes and peroxides, which are known as substances harmful to hydroformylation catalyst, are removed.

As the catalyst, there may be normally used a catalyst made of a transition metal belonging to the group VIII in the periodic table comprising an organic phosphorus compound as a coordinate. As the metal belonging to the group VIII, there may be normally used rhodium, cobalt, iridium or the like, preferably rhodium. As the rhodium source, there may be used a rhodium complex such as hydride carbonyl tris(triphenylphosphine)rhodium and acetoxy bis (triphenylphosphine)rhodium. Besides these rhodium complexes, oxides such as rhodium acetylactonate and rhodium acetate may be used.

The organic phosphorus compound to be used herein is not specifically limited.

Examples of the organic phosphorus compound employable herein include cyclic and/or noncyclic trialkylphosphines such as tributyl phosphine, trioctyl phosphine, tricyclohexyl phosphine and butyldicyclohexyl phosphine, cyclic and/or noncyclic alkylaryl phosphines such as monobutyldiphenyl phosphine, dipropylphenyl phosphine and cyclohexylphenyl phosphine, triaryl phosphines such as triphenyl phosphine, tritolyl phosphine and triphenyl phosphine having a hydrogen atom on the phenyl group substituted by a sulfone group, halogen atom or the like, cyclic and/or noncyclic trialkyl phosphites such as trioctyl phosphite and tricyclohexyl phosphite, triaryl phosphites such as triphenyl phosphite and trinaphthyl phosphite which may have substituents, and alkylaryl phosphite. Further, compounds as ldisclosed in U.S. Pat. Nos. 3,415,906, 4,599,206, 4,351, 759, 4,748,261, 4,567,306, 5,235,113 and 5,227,532 may be used.

Two or more of these organic compounds may be used in admixture as a coordinate. Alternatively, the foregoing organic phosphorus compound and a pentavalent organic phosphorus compound such as triphenylphosphine oxide may be used in admixture as a coordinate.

Referring to the process for the preparation of the catalyst, the rhodium source and the organic phosphorus compound as a coordinate may be separately supplied into the hydroformylation reactor so that a catalyst is produced in the reaction system. Alternatively, the rhodium source may be previously treated with carbon monoxide and hydrogen at a high temperature and a constant pressure in a solvent together with the organic phosphorus compound as a coordinate outside the reactor to prepare a catalyst solution. The solvent to be used in the preparation of such a catalyst may be normally selected from the group consisting of the reaction solvents described later but may be different from the reaction solvent. The concentration of rhodium in the solution from which the catalyst is prepared is normally from 1 to 100,000 ppm. The amount of the organic phosphorus compound to be added as a coordinate is from 1 to 10,000 mols per atom of rhodium as calculated in terms of phosphorus atom. The treatment temperature is from 60° C. to 200° C. The treatment pressure is from ordinary pressure to 200 kg/cm$^2$. The treatment time is from 0.01 to 20 hours. The vessel for use in the foregoing treatment may be either batchwise or continuous.

As the reaction solvent for use in the hydroformylation there may be used the olefin itself. Alternatively, the aldehyde thus produced or the high boiling compound produced subsidiarily during the reaction may be used. Besides these solvents, various solvents which can dissolve the catalyst therein and have no adverse effects on the reaction may be used such as an aliphatic hydrocarbon (e.g., hexane, octane), an aromatic hydrocarbon (e.g., toluene, xylene), an alcohol (e.g., butanol, 2-ethylhexanol, ethylene glycol, propylene glycol), an ether (e.g., triglyme), an ester (e.g., dioctyl phthalate) and water.

The pressure at which the mixture of hydrogen and carbon monoxide undergoes a hydroformylation reaction is normally from 0.1 to 300 kg/cm$^2$. The ratio of hydrogen partial pressure to carbon monoxide partial pressure is from 0.1 to 10. The reaction temperature is from 60° C. to 200° C. The concentration of rhodium in the reaction solution is from 1 to 100,000 ppm. The amount of the organic phosphorus compound to be added as a coordinate is from 1 to 10,000 mols per atom of rhodium as calculated in terms of phosphorus atom. The reaction time is from 0.01 to 20 hours.

The foregoing process for obtaining an aldehyde as a product from the hydroformylation reaction zone is not specifically limited. In practice, however, a method involving gas stripping as described in JP-A-52-125103 or a method involving distillation as described in JP-A-54-89974 may be used. Whichever method is used, a catalyst solution containing the majority of unreacted olefin, solvent and high boiling by-products can be removed as a result. Accordingly, the aldehyde compound obtained by the foregoing methods contains an aldehyde as a main component as well as an extremely small amount of dissolved gases (e.g., hydrogen, carbon monoxide, methane, carbon dioxide), a small amount of unreacted olefins and paraffins which are lighter in weight than the aldehyde, a small amount of water content, a small amount of fractions having carbon atoms in an amount of one less than that of the aldehyde as a main component and having a lighter weight than the aldehyde, and a small amount of solvent and high boiling by-products.

The aldehyde obtained from the hydroformylation reaction zone contains a straight-chain aldehyde and a branched aldehyde. If necessary, the straight-chain aldehyde may be separated, purified, and then used at the subsequent step, i.e., the hydrogenation reaction step or condensation step. If the branched aldehyde occurs in an extremely small amount or if the branched aldehyde or impurities derived therefrom can be fully separated and removed at a separation step following the hydrogenation reaction step, the straight-chain aldehyde and the branched aldehyde may be together carried to the subsequent step. For the separation and purification of the straight-chain aldehyde, the separation process is not limited if the straight-chain aldehyde and the branched aldehyde can be directly separated from each other. For example, if distillation is used for separation, the pressure at the top of the distillation column is not specifically limited. However, if distillation is effected under reduced pressure, the resulting undercondensation causes loss of aldehyde. Accordingly, the pressure at the top of the distillation column is preferably not lower than the atmospheric pressure. The temperature in the distillation column varies with the pressure at the bottom of the distillation column determined by the number of carbon atoms contained in the aliphatic aldehyde, the pressure at the top of the distillation column and the kind of the distillation column used. It is preferably from 60° C. to 120° C. at the top of the distillation column or from 70° C. to 150° C. at the bottom of the distillation column.

The aldol condensation reaction of the aldehyde produced by the foregoing hydroformylation reaction may be effected in either liquid phase or gas phase. If the aldol condensation reaction is effected in a liquid phase, the liquid phase is normally an alkaline aqueous solution such as an aqueous solution of caustic soda. The reaction temperature is from 80° C. to 120° C. The reaction pressure may not be lower than the saturated pressure of the solution at the predetermined temperature, preferably from ordinary temperature to 10 kg/cm$^2$.

In order to subject the aldehyde obtained by the hydroformylation reaction and the polycondensed aldehyde obtained by the aldol condensation of the aldehyde, e.g., butyraldehyde obtained by the hydroformylation reaction of propylene, and 2-ethyl-2-hexenal as an aldol condensate thereof to a mixing hydrogenation reaction, the hydrogenation catalyst and reaction conditions may be arbitrarily selected from the group consisting of those used in known commonly used methods.

The hydrogenation catalyst employable herein is not specifically limited so far as it can catalyze the hydrogenation reaction of the aldehyde. In practice, however, a catalyst containing a metal belonging to group VIII such as nickel, palladium and platinum, a solid catalyst containing a reducing mixture of copper oxide and zinc oxide, a copper-chromium catalyst, copper-chromium-manganese-barium catalyst or the like may be used. Further, an improved catalyst comprising a mixture of copper oxide and zinc oxide as described in Japanese Patent No. 2,655,034 may be used.

In the present invention, the mixing ratio of the aldehyde to be supplied as a starting material into the hydrogenation reaction system together with its condensate is from 95:5 to 5:95, preferably from 10:1 to 1:10, more preferably from 10:3 to 3:10 by weight as calculated in terms of ratio of aldehyde having from 2 to 5 carbon atoms to polycondensate thereof. If the aldehyde having from 2 to 5 carbon atoms and the aldehyde polycondensate are used in amounts outside the above mixing ratio, the resulting effect of inhibiting the production of an ester and ether comprising two or more molecules of aldehyde polycondensate bonded thereto is remarkably lessened to disadvantage.

The mixing hydrogenation reaction of the aldehyde as a starting material may be effected in either liquid phase or gas phase. In practice, however, the mixing hydrogenation reaction in the gas phase is preferably effected because the production of ether-based by-products can be inhibited as compared with the mixing hydrogenation reaction in the liquid phase. The hydrogenation reaction conditions are not specifically limited. In practice, however, the reaction temperature is from 50° C. to 300° C., preferably from 100° C. to 250° C., more preferably from 150° C. to 200° C. The hydrogen pressure is from ordinary pressure to 200 kg/cm$^2$, preferably from ordinary pressure to 100 kg/cm$^2$, more preferably from ordinary pressure to 10 kg/cm$^2$. The reaction process may be either batchwise or continuous.

The reaction solution produced by the foregoing mixing hydrogenation reaction may be subjected to separation and purification to individual alcohols by any known common method such as distillation. One of the alcohols thus produced is a monomer while the other is a polycondensate. Accordingly, when one aldehyde and the polycondensate of the aldehyde is subjected to the mixed hydrogenation, the two alcohols have greatly different boiling points and thus can be easily separated from each other. For example, the boiling point of n-butyl alcohol is 117.7° C. while that of 2-ethylhexanol is 183.5° C.

The alcohol obtained according to the process of the present invention can be subjected to an esterification reaction with a carboxylic acid or carboxylic anhydride to produce an ester compound which can then be used as a plasticizer for a resin. Examples of the carboxylic acid or carboxylic anhydride that can be used in the foregoing esterification reaction include phthalic acid, phthalic anhydride, adipic acid, azelaic acid, sebacic acid, trimellitic acid, trimellitic anhydride, pyromellitic acid, and pyromellitic anhydride. Preferred among these compounds are phthalic acid and phthalic anhydride. The esterification reaction may be carried out by any known commonly used method. For example, the alcohol and the carboxylic acid may be reacted in the presence of a catalyst (see Koichi Murai, "Plasticizer—Its Theory and Application-", Saiwai Shobo, pp. 415–426, Mar. 1, 1973). The ester compound thus obtained can be added as a plasticizer to a vinyl such as polyvinyl chloride (see Koichi Hurai, "Plasticizer—Its Theory and Application-", Saiwai Shobo, pp. 481–536, Mar. 1, 1973).

EXAMPLES

Having generally described this invention, a further understanding can be obtained by reference to certain specific examples which are provided herein for purposes of illustration only and are not intended to be limiting unless otherwise specified.

Example 1

Into an SUS monotube reactor having a size of 1 inch-diameter×60 cm-height filled with 10 cc of a columnar Cu-Cr hydrogenation catalyst having a size of 5 mm-diameter×5 mm-height (trade name: N202E, produced by Nikki Chemical Co., Ltd. ) were supplied 2-ethyl-2-hexenal (hereinafter referred to as "EPA") in vaporized form, n-butyraldehyde (hereinafter referred to as "NBD") in vaporized form and hydrogen at a rate of 68.35 mmol/Hr, 45.74 mmol/Hr and 2,400 mmol/Hr, respectively. Under these conditions, these components were subjected to a gas phase hydrogenation reaction at a reaction pressure of 4.6 kg/cm$^2$G (as indicated by a pressure indicator) and a reaction temperature of 1 80° C. The resulting reaction solution (condensation solution from the exit of the reactor) was then analyzed by gas chromatography. The weight ratio of EPA to NBD during supply was 72:28. The results are set forth in Table 1. The catalyst in the reactor had been previously reduced at a temperature of 200° C. in a dilute stream of hydrogen containing nitrogen as a diluent.

Comparative Example 1

The procedure of Example 1 was followed except that only EPA was supplied as starting material aldehyde at a rate of 103.8 mmol/Hr. The results are set forth in Table 1.

Comparative Example 2

The procedure of Example 1 was followed except that only NBD was supplied as starting material aldehyde at a rate of 107.6 mmol/Hr. The results are set forth in Table 1.

TABLE 1

|  |  | Example 1 | Comparative Example 1 | Comparative Example 2 |
|---|---|---|---|---|
| EPA:NBD weight ratio | EPA | 72 | 100 | 0 |
|  | NBD | 28 | 0 | 100 |
| Conversion (%) | EPA | 100 | 100 | — |
|  | NBD | 99.90 | — | 99.95 |
| Yield (%) | 2EH | 99.83 | 99.40 | — |
|  | NBA | 99.90 | — | 97.05 |
|  | Ester 1 | 0.212 | 0.384 | — |
|  | Ester 2 | 0.0219 | — | 0.525 |
|  | By-product | 0.0 | 0.22 | 2.42 |

Description of Abbreviation:
  2EH: 2-Ethylhexanol
  EPA: 2-Ethyl-2-hexenal
  Ester 1: 2-Ethylhexanoic acid-2-ethylhexyl
  Ester 2: Butyl butyrate
  NBA: n-Butyl alcohol
  NBD: n-Butyraldehyde
  By-product: Other by-products

Example 2

A columnar Cu-Cr hydrogenation catalyst having a size of 5 mm-diameter×5 mm-height (trade name: N202E, produced by Nikki Chemical Co., Ltd.) was ground to a size of from 16 to 24 mesh. Into an SUS monotube reactor having a size of 8 mm-diameter×60 cm-height filled with 7.4 cc of the foregoing catalyst were supplied EPA in vaporized form, NBD in vaporized form and hydrogen at a rate of 90 mmol/Hr, 105 mmol/Hr and 13,300 mmol/Hr, respectively, a reaction temperature of 180° C. and a reaction pressure of 4 kg/m$^2$G (as indicated by a pressure indicator). The weight ratio of EPA to NBD during supply was 60:40. The catalyst in the reactor had been previously reduced at a temperature of about 200° C. in a dilute stream of hydrogen containing nitrogen as a diluent. The resulting condensation solution from the exit of the reactor was then analyzed by gas chromatography. The results are set forth in Table 2.

Example 3

The procedure of Example 2 was followed except that the rate at which EPA and NBD were supplied into the reaction system as starting material aldehyde were 74 mmol/Hr and 130 mmol/Hr, respectively. The weight ratio of EPA to NBD during supply was 50:50. The results are set forth in Table 2.

Example 4

The procedure of Example 2 was followed except that the rate at which EPA and NBD were supplied into the reaction system as starting material aldehyde were 175 mmol/Hr and 34 mmol/Hr, respectively. The weight ratio of EPA to NBD during supply was 90:10. The results are set forth in Table 2.

Comparative Example 3

A columnar Cu-Cr hydrogenation catalyst having a size of 5 mm-diameter×5 mm-height (trade name: N202E, produced by Nikki Chemical Co., Ltd.) was ground to a size of from 16 to 24 mesh. Into an SUS monotube reactor having a size of 8 mm-diameter×60 cm-height filled with 7 cc of the foregoing catalyst were supplied NBD in vaporized form and hydrogen at a rate of 233 mmol/Hr and 13,000 mmol/Hr, respectively, a reaction temperature of 170° C. and a reaction pressure of 4 kg/cm$^2$G (as indicated by a pressure indicator). The catalyst in the reactor had been previously reduced at a temperature of 200° C. in a dilute stream of hydrogen containing nitrogen as a diluent. The resulting condensation solution from the exit of the reactor was then analyzed by gas chromatography. The results are set forth in Table 2.

TABLE 2

|  |  | Example 2 | Example 3 | Example 4 | Comparative Example 3 |
|---|---|---|---|---|---|
| EPA:NBD weight ratio | EPA | 60 | 50 | 90 | 0 |
|  | NBD | 40 | 50 | 10 | 100 |
| Conversion (%) | EPA | 99.99 | 100.00 | 99.98 |  |
|  | NBD | 99.92 | 99.90 | 99.95 | 99.88 |
| Yield (%) | Ester 1 | 0.01 | 0.01 | 0.03 |  |
|  | Ester 2 | 0.01 | 0.02 | 0.01 | 0.48 |
|  | By-Product | 0.0 | 0.0 | 0.0 | 0.11 |

Description of Abbreviation:
  EPA: 2-Ethyl-2-hexenal
  Ester 1: 2-Ethylhexanoic acid-2-ethylhexyl
  Ester 2: Butyl butyrate
  NBD: n-Butyraldehyde
  By-product: Other by-products In accordance with the process of the present invention, by supplying an aldehyde having from 2 to 5 carbon atoms and a polycondensate thereof at a predetermined mixing ratio into the same reaction system where they are then subjected to a mixing hydrogenation reaction, the production of an ester and/or ether as by-products can be inhibited as compared with the conventional single hydrogenation reaction. Further, the percent production of alcohols corresponding to the aldehydes supplied as starting materials can be enhanced. Moreover, two series of reactors have heretofore been required. In accordance with the present invention, the number of series of reactors can be reduced to one. Accordingly, the present invention has an extremely great industrial value.

While the above invention has been described in terms of "a mixture comprising an aldehyde having from 2 to 5 carbon atoms and a polycondensate of the aldehyde", it is understood that the invention applies also to a mixture comprising (1) at least one aldehyde having from 2 to 5 carbon atoms, and (2) polycondensates of each of the aldehydes included in (1). In the present claims, the term "a mixture comprising an aldehyde having from 2 to 5 carbon atoms and a polycondensate of the aldehyde", is intended to include the embodiment of more than one such aldehyde, and more than one concomitant polycondensate.

The entire disclosure of Japan priority document application JP 337351/1998, filed Nov. 27, 1998, is hereby incorporated by reference.

What is claimed is:

1. A process for producing alcohols, which comprises:
   subjecting a mixture comprising a) one aldehyde selected from the group consisting of aldehydes having from 2 to 5 carbon atoms and b) a polycondensate of the aldehyde at a weight ratio of from 95:5 to 5:95 to a mixing hydrogenation reaction in the presence of a catalyst to produce alcohols corresponding to the aldehydes at the same time;
   wherein said polycondensate of the aldehyde is a dimer obtained by aldol condensation;
   wherein the mixing hydrogenation reaction is carried out in a gas phase;
   wherein substantially no by-product is produced.

2. The process according to claim 1, wherein the weight ratio of the aldehyde having from 2 to 5 carbon atoms to the polycondensate of the aldehyde is from 10:1 to 1:10.

3. The process according to claim 1, wherein the weight ratio of the aldehyde having from 2 to 5 carbon atoms to the polycondensate of the aldehyde in from 10:3 to 3:10.

4. The process according to claim 1, wherein the aldehyde has 4 carbon atoms.

5. The process according to claim 1, wherein the aldehyde is produced by hydroformylation of an olefin.

6. The process according to claim 1, wherein said mixture is supplied into the same reaction system prior to said subjecting said mixture to said mixing hydrogenation reaction.

7. The process according to claim 1, wherein only one aldehyde having from 2 to 5 carbon atoms is present.

8. A process for producing alcohols, which comprises subjecting a mixture of 2-ethyl-2-hexenal and butyraldehyde to a hydrogenation reaction in the presence of a catalyst to produce 2-ethylhexanol and butyl alcohol at the same time, wherein the 2-ethyl-2-hexenal and butyraldehyde are present in a weight ratio of from 95:5 to 5:95;
   wherein said 2-ethylhexanol and said butyl alcohol are obtained in yields of at least 99.83% without any by-product.

9. The process according to claim 8, wherein the weight ratio of 2-ethyl-2-hexenal to butyraldehyde is from 10:1 to 1:10.

10. The process according to claim 8, wherein the weight ratio of 2-ethyl-2-hexenal butyraldehyde is from 10:3 to 3:10.

11. The process according to claim 8, wherein the hydrogenation reaction is carried out in a gas phase.

12. The process according to claim 8, wherein the butyraldehyde is produced by hydroformylation of a propylene.

13. A process for producing alcohols, which comprises:
   subjecting an olefin having 4 or less carbon atoms to hydroformylation with hydrogen and carbon monoxide in the presence of a catalyst to obtain an aldehyde;
   subjecting a part of the aldehyde to aldol condensation to produce a dimer;
   subjecting the aldehyde and the aldol condensation dimer at a weight ratio of from 95:5 to 5:95, in the same reaction system, to a mixing hydrogenation reaction to produce alcohols corresponding to the aldehyde and the aldol condensation dimer at the same time; and
   isolating each of the alcohols by a separator;
   wherein substantially no by-product is produced.

14. The process according to claim 13, wherein the weight ratio of the aldehyde to the aldol condensation dimer is from 10:1 to 1:10.

15. The process according to claim 13, wherein the weight ratio of the aldehyde to the aldol condensation dimer is from 10:3 to 3:10.

16. The process according to claim 13, wherein the olefin is a propylene and the aldol condensation dimer is 2-ethyl-2-hexenal.

17. The process according to claim 13, wherein the mixing hydrogenation reaction is carried out in a gas phase.

18. A process for producing a carboxylic acid ester, which comprises reacting an alcohol produced by the process according to claim 13 with a carboxylic acid or a carboxylic anhydride.

19. The process according to claim 18, wherein the carboxylic acid ester is a phthalic acid ester, and the carboxylic acid or carboxylic anhydride is phthalic acid or phthalic anhydride.

* * * * *